(12) United States Patent
Benoit

(10) Patent No.: US 7,285,129 B2
(45) Date of Patent: Oct. 23, 2007

(54) HIGH EFFICIENCY TANNING APPARATUS

(76) Inventor: David James Benoit, 60 Cabral Dr., Middleton, MA (US) 01949

( * ) Notice: Subject to any disclaimer, the term of this patent is extended or adjusted under 35 U.S.C. 154(b) by 466 days.

(21) Appl. No.: 10/922,201

(22) Filed: Aug. 20, 2004

(65) Prior Publication Data
US 2006/0041290 A1 Feb. 23, 2006

(51) Int. Cl.
*A61N 5/06* (2006.01)
(52) U.S. Cl. .......................... 607/94; 128/898; 607/88; 250/504 R
(58) Field of Classification Search ............ 250/504 R; 607/94; 128/898
See application file for complete search history.

(56) References Cited

U.S. PATENT DOCUMENTS

| | | | |
|---|---|---|---|
| 2,806,148 A * | 9/1957 | Barton, Jr ................ 250/565 |
| 3,149,271 A * | 9/1964 | Smith, Jr. ................ 318/620 |
| 4,171,484 A * | 10/1979 | Hunt ........................ 378/108 |
| 4,665,627 A * | 5/1987 | Wilde et al. ............... 34/278 |
| 4,888,526 A | 12/1989 | Nilssen | |
| 4,896,078 A | 1/1990 | Nilssen | |
| 4,972,126 A | 11/1990 | Nilssen | |
| 5,040,236 A * | 8/1991 | Costello ................... 392/417 |
| 5,374,825 A | 12/1994 | Doty et al. | |
| 5,557,112 A | 9/1996 | Csoknyai et al. | |
| 5,565,685 A | 10/1996 | Czako et al. | |
| 5,712,485 A | 1/1998 | Broer et al. | |
| 5,957,959 A | 9/1999 | Rissmaney et al. | |
| 6,265,835 B1 * | 7/2001 | Parra ........................ 315/246 |
| 6,494,901 B1 | 12/2002 | Doty | |
| 6,660,025 B2 | 12/2003 | Versemann et al. | |
| 6,825,620 B2 * | 11/2004 | Kuennen et al. ............ 315/224 |
| 2003/0015479 A1 * | 1/2003 | Kuennen et al. ............ 210/748 |

FOREIGN PATENT DOCUMENTS

DE 19912517 A1 * 9/2000
JP 2000340478 A * 12/2000

* cited by examiner

*Primary Examiner*—Henry M Johnson, III
(74) *Attorney, Agent, or Firm*—Edwards Angell Palmer & Dodge LLP

(57) ABSTRACT

Tanning apparatuses and methods of operating tanning apparatuses for high efficiency use. In an embodiment, a tanning apparatus including a tanning lamp is operated by delivering a first input voltage to the tanning lamp to generate an ultraviolet radiation output. When the output from the tanning lamp has sufficiently decreased over time due to use, the first input voltage is increased to increase the output to an effective level. Preferably, a variable voltage transformer is used to increase input voltage.

10 Claims, 1 Drawing Sheet

HIGH EFFICIENCY TANNING APPARATUS

FIELD OF THE INVENTION

The present invention relates to tanning apparatuses, and more particularly, to tanning apparatuses that include means for controlling the energy delivered to such apparatuses for increased efficiency.

BACKGROUND

Tanning apparatuses such as booths and beds represent a popular and growing industry estimated at $7 billion as of 2003. A major component of tanning apparatuses is the fluorescent lamp used to deliver ultraviolet ("UV") radiation to a user. Other types of lamps used in related applications include high pressure lamps, facial lamps, and quartz high pressure lamps. Such lamps mimic the effects of the sun to effectively tan the skin of a user by delivering a combination of UVA and UVB radiation while filtering out UVC, the most harmful UV radiation emitted by the sun. All fluorescent lamps share the same basic design: a glass tube lined with a coating of phosphors, electrodes on the inside, and end caps at each end to seal the lamp. The tube contains mercury vapor gas under low pressure, which is ionized upon exposure to an electric current. UV emissions result from the energy transfer between electrons in a supplied current and the mercury gas atoms. The most prevalent lamps in the tanning industry generally exceed the natural intensity of the sun by two to five times.

Tanning lamps are characterized by a useful lifetime in which they deliver an effective dose of ultraviolet radiation while remaining within the safe voltage range specified by the tanning apparatus or lamp manufacturer. Commercially available fluorescent lamps intended for use in tanning apparatuses are typically quoted to have a useful lifetime as long as 1000 hours or more. In practice, however, it is not uncommon for lamps to last for only a percentage of advertised lifetime. One of the reasons for this limitation is that lamps are often operated at a relatively high voltage to ensure that UV emission is sufficient to ensure an effective result to the user. High voltages can raise the operating temperature of the lamp, thereby shortening lamp life.

Some users employ voltage transformers known as "buck boosters" to bring their tanning apparatuses within specified voltage ratings. A buck booster will either increase or decrease the incoming voltage so it will be at a level that the tanning apparatus was designed to utilize. Buck boosters operate as step transformers such that they are only able to increase or decrease the incoming voltage by a pre-set number of volts, or by a pre-set percentage of incoming voltage. For example, common buck boosters are sold in a +/−16/32 or +/−12/24 configuration, meaning that they can increase or decrease voltage 16 or 32 volts or 12 or 24 volts, respectively. These units are used without regard to the UV delivery efficiency of the lamps used in a tanning apparatus, but rather are used to simply bring the operating voltage to within manufacturer specifications.

The inventor has recognized that conventional tanning apparatuses and related operation methods are inefficient. The use of unnecessarily high operating voltages to maximize the delivered UV dose results in a drastic decrease in lamp life. The use of buck boosters is inefficient because they impose an arbitrary step in voltage without regard to UV dose. Moreover, regardless of whether a buck booster is used, conventional tanning apparatus operating methods make use of a static voltage throughout the life of a tanning lamp. If this single voltage is too high, lamp life can be compromised; if too low, efficient tanning results will not be obtained.

Recognizing the shortcomings of conventional tanning apparatuses and operating methods, there is a need for efficient and cost effective apparatuses and methods in which operating voltage is precisely and dynamically controlled for enhanced operating efficiencies. Relatedly, there is a need to control the output of tanning lamps so that it is generally constant over the lamp lifetime.

SUMMARY OF THE INVENTION

In one aspect, the present invention is a method of operating any apparatus that includes a lamp that degrades over time. In another aspect, the present invention is a method of operating a tanning apparatus to yield an efficient and cost-effective result. In another aspect, the present invention is a tanning apparatus that includes means for regulating an input voltage supplied to tanning lamps such that the input voltage is increased over time as UV output decreases due to use.

In one embodiment, the method of the present invention comprises providing a tanning apparatus that includes a tanning lamp, delivering a first input voltage at a first time point to the tanning lamp to generate an ultraviolet radiation output, and increasing the first input voltage to a second input voltage at a second, later time point in response to a decrease in the ultraviolet radiation output.

In another embodiment, the method of the present invention comprises providing a tanning apparatus that includes a tanning lamp, delivering a first input voltage to the tanning lamp, measuring the first input voltage at a first time point, decreasing the first input voltage to a second input voltage sufficient for the tanning lamp to generate an ultraviolet radiation output that is sufficient to effectively tan the skin of a user, monitoring the ultraviolet radiation output over time, and increasing the second input voltage to a third input voltage at a second time point in response to a decrease in the ultraviolet radiation output of the tanning lamp.

In yet another embodiment, the invention is a tanning apparatus comprising a voltage supply, a tanning lamp electrically connected to the voltage supply, a sensor to measure an ultraviolet radiation output of the tanning lamp over time, and means to control the voltage supplied to the tanning lamp.

In certain preferred embodiments, a variable voltage transformer is used to control the input voltage supplied to the tanning lamps of the invention.

In certain other embodiments, the input voltage to the tanning lamps of the present invention is automatically triggered by a decrease in ultraviolet radiation output to a predetermined level.

One advantage of the present invention is that it yields a high efficiency tanning apparatus and procedure, thus extending tanning lamp life.

Another advantage of the present invention is that it provides for a high degree of control over the power delivered to tanning apparatuses.

Another advantage of the present invention is that it provides for the ability to deliver a substantially constant UV output over time notwithstanding bulb degradation.

Another advantage of the present invention is that it provides a cost-effective means of operating tanning apparatuses.

Yet another advantage of the present invention is that it provides for the delivery of an optimal voltage to a tanning apparatus to provide for a desirable balance between lamp life and user results.

PREFERRED EMBODIMENTS

Figure 1:
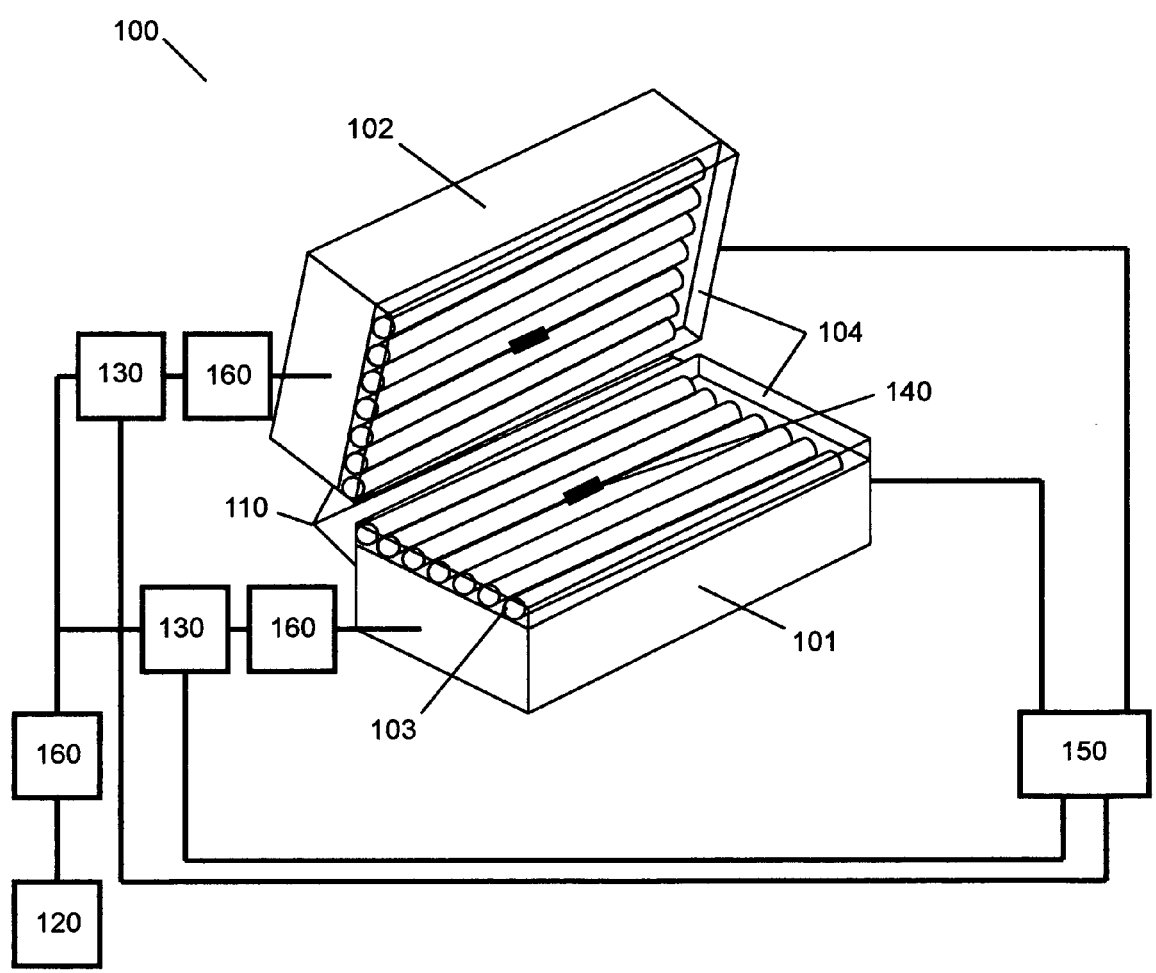
FIG. 1 is a perspective view of a preferred embodiment of the present invention.

The present invention includes high efficiency tanning apparatuses and operation methods. While the present invention is described with specific reference to tanning apparatuses, it is intended that the invention include any apparatus, and methods of operation thereof, that includes a lamp that degrades over time. Such an apparatus may be used, for example, in greenhouses or for general lighting purposes. As used herein, a "tanning apparatus" is intended to include any instrument that includes at least one tanning lamp for the delivery of UV radiation to a user to thus tan the user's skin. A "tanning lamp" is any lamp, bulb, or tube that emits UV radiation, preferably a combination of UVA and UVB radiation, including fluorescent lamps, high pressure lamps, facial lamps, and quartz high pressure lamps. The "ultraviolet radiation output" of a tanning lamp is used to define its effective dose or output, usually measured in mW/cm2. While not intending to limit the present invention, it is further described herein with reference to its preferred embodiments.

A tanning bed embodiment of the present invention is shown in FIG. 1. Bed 100 includes a bench portion 101 and a canopy portion 102 attached by a hinge means 110. Each of bench portion 101 and canopy portion 102 includes a bank of elongated, tubular fluorescent tanning lamps 103 arranged within ballasts, as is known in the art. An acrylic window 104 is placed over the tanning lamps 103 in each of the bench and canopy portions 101, 102. The configuration of bench and canopy portions is designed to form a space to accommodate a user therein.

A power supply 120 provides power to the tanning lamps 103. One or more variable voltage transformers 130 are used to regulate the voltage delivered from the power supply 120 to the tanning lamps 103. In one embodiment, the bench and canopy portions 101, 102 are in electrical connection and a single variable voltage transformer 130 is used to regulate the voltage delivered to both. In another embodiment, power is separately delivered to the bench and canopy portions 101, 102, and separate variable voltage transformers 130 are used to regulate the voltage delivered to each.

Variable voltage transformers are known in the electrical arts. Unlike standard fixed ratio transformers like buck boosters, variable voltage transformers are designed to provide a variable output voltage adjustable from 0 to over 100 percent of input voltage. Variable voltage transformers are commercially available from sources such as Superior Electric (Bristol, Conn.).

When in operation, power supply 120 provides power to tanning lamps 103 so that they emit ultraviolet radiation. As is known in the art, tanning lamps 103 are typically rated by bed manufacturers for an acceptable voltage input range. When the tanning lamps 103 are new and therefore provide a relatively high ultraviolet radiation output for a given input voltage, the variable voltage transformer 130 is used to specify an input voltage at or near the low end of the acceptable voltage input range. As the tanning lamps 103 degrade over time such that their ultraviolet radiation output decreases for a given input voltage, the variable voltage transformer 130 is used to specify an increasingly higher input voltage within the acceptable voltage input range.

In a preferred embodiment, the decrease in the ultraviolet radiation output of the tanning lamps 103 is monitored over time, and the input voltage correspondingly increased with the use of the variable voltage transformer(s), so that the ultraviolet radiation output is substantially constant throughout the lifetime of the lamps. The result is that the tanning lamps 103 provide substantially the same dose of ultraviolet radiation to subsequent users over time.

The ultraviolet radiation output may be monitored with the use of a commercially available ultraviolet radiation meter, such as a spectroradiometer or solarmeter. The desired frequency of monitoring the output will depend on the rate at which the tanning lamps 103 degrade over time. For most commercially available tanning lamps, it is recommended that the ultraviolet radiation output be monitored at least weekly. In a preferred embodiment, one or more ultraviolet radiation meters 140 are integral to the tanning apparatus 100 and provide continuous feedback to a computer 150 or other means capable of automatically controlling the variable voltage transformer(s) 130.

Some preferred embodiments of the present invention include one or more voltmeters 160 to monitor the voltage delivered to the tanning lamps 103. When multiple tanning apparatuses are used together such as in a tanning salon, it is not uncommon for voltage to fluctuate due to salon load increase or decrease. The use of voltmeters 160, placed either before or after the variable voltage transformer(s) 130, enable the monitoring of such voltage fluctuations. Further, it is preferred that when voltmeters 160 are used, the variable voltage transformers used in the present invention are motorized variable voltage transformers, which are manipulated by a chain system or the like, as known in the art. In this embodiment, the voltmeters 160 and the motorized variable voltage transformers 130 are in electrical connection such that the voltmeters 160 provide feedback to the motorized variable voltage transformers 130 to keep the voltage delivered to the tanning lamps 103 at the desired level regardless of voltage fluctuations provided by power supply 120.

In all embodiments of the present invention, the voltage delivered to the tanning lamps 103 is gradually increased over time until it reaches a level that is at or near the high end of the acceptable voltage input range for the lamps used. When lamps are no longer capable of providing a useful ultraviolet radiation output at the high end of the acceptable voltage input range, the lamps are discarded in favor of new ones.

It will be obvious to those skilled in the art, having regard to this disclosure, that other variations on this invention beyond those specifically exemplified here may be made. Such variations are, however, to be considered as coming within the scope of this invention as limited solely by the following claims.

I claim:

1. A method of operating a tanning apparatus, comprising the steps of:

providing a tanning apparatus comprising a tanning lamp;
delivering a first input voltage to said tanning lamp;
measuring said first input voltage at a first time point;
decreasing said first input voltage to a second input voltage at substantially said first time point, said second input voltage being sufficient for said tanning lamp to generate an ultraviolet radiation output sufficient to effectively tan the skin of a user of said tanning apparatus;

monitoring said ultraviolet radiation output over time; and increasing said second input voltage to a third input voltage at a second time point in response to a decrease in said ultraviolet radiation output of said tanning lamp, said second time point occurring after said first time point.

2. The method of claim 1, wherein said step of increasing the second input voltage comprises using a variable voltage transformer.

3. The method of claim 1, wherein said step of delivering a first input voltage generates a first ultraviolet radiation output, and said step of increasing said second input voltage to a third input voltage generates an ultraviolet radiation output that is substantially equivalent to said first ultraviolet radiation output.

4. The method of claim 1, wherein said step of increasing said second input voltage comprises using a motorized variable voltage transformer.

5. The method of claim 1, wherein said step of increasing said second input voltage comprises using a motorized variable voltage transformer in electrical connection to a voltmeter used to monitor said first input voltage.

6. The method of claim 1, wherein said step of providing a tanning apparatus comprising a tanning lamp comprises providing a tanning bed.

7. The method of claim 1, wherein said step of providing a tanning apparatus comprising a tanning lamp comprises providing a tanning bed comprising a bench portion and a canopy portion.

8. The method of claim 1, wherein said step of providing a tanning apparatus comprising a tanning lamp comprises providing a tanning bed comprising a bench portion and a canopy portion, said canopy portion comprising multiple said tanning lamps in electrical connection to a first variable transformer.

9. The method of claim 1, wherein said step of providing a tanning apparatus comprising a tanning lamp comprises providing a tanning bed comprising a bench portion and a canopy portion, said canopy portion comprising multiple said tanning lamps in electrical connection to a first variable transformer and said bench portion comprising multiple said tanning lamps in electrical connection to a second variable voltage transformer.

10. The method of claim 1, wherein said step of providing a tanning apparatus comprising a tanning lamp comprises providing a tanning booth.

\* \* \* \* \*